US011249007B2

(12) United States Patent
Deng

(10) Patent No.: US 11,249,007 B2
(45) Date of Patent: Feb. 15, 2022

(54) UNIVERSAL STRIP TRIBOLOGICAL SIMULATOR

(71) Applicant: Aleris Rolled Products, Inc., Beachwood, OH (US)

(72) Inventor: Zhi Deng, Northville, MI (US)

(73) Assignee: COMMONWEALTH ROLLED PRODUCTS, INC., New York, NY (US)

(*) Notice: Subject to any disclaimer, the term of this patent is extended or adjusted under 35 U.S.C. 154(b) by 0 days.

(21) Appl. No.: 15/733,539

(22) PCT Filed: Mar. 14, 2019

(86) PCT No.: PCT/US2019/022181
§ 371 (c)(1),
(2) Date: Aug. 24, 2020

(87) PCT Pub. No.: WO2019/182845
PCT Pub. Date: Sep. 26, 2019

(65) Prior Publication Data
US 2020/0408671 A1 Dec. 31, 2020

Related U.S. Application Data

(60) Provisional application No. 62/645,290, filed on Mar. 20, 2018.

(51) Int. Cl.
*G01N 19/02* (2006.01)
*G01N 3/08* (2006.01)
(52) U.S. Cl.
CPC .............. *G01N 19/02* (2013.01); *G01N 3/08* (2013.01); *G01N 2203/0023* (2013.01)
(58) Field of Classification Search
CPC ............. G01N 2203/0023; G01N 3/24; G01N 2203/0073; G01N 2203/0005;
(Continued)

(56) References Cited

U.S. PATENT DOCUMENTS 1,413,305 A * 4/1922 Webb ...................... G01N 3/00
73/838
3,324,714 A * 6/1967 Simon ...................... G01N 3/20
73/853
(Continued)

FOREIGN PATENT DOCUMENTS

CN 204359623 5/2015
EP 1091204 A2 * 4/2001 ............. G01N 19/02
(Continued)

OTHER PUBLICATIONS

R.H. Wagoner et al., Development of OSU formability test and OSU friction test, Journal of Materials Processing Technology, vol. 45, No. 1-4, Sep. 1, 1994, pp. 13-18, XP055769829.
(Continued)

*Primary Examiner* — David A. Rogers
(74) *Attorney, Agent, or Firm* — Vorys, Sater, Seymour and Pease LLP

(57) ABSTRACT

A tribological testing simulator includes a base having a pair of catchers that clamp onto a specimen, a punch that is drawn through the specimen, and a plurality of sensors that take measurements of respective regions of the specimen. The sensors measure their respective regions of the specimen as it is drawn from an un-deformed state to a deformed state, and facilitate conducting a tensile strip friction test. In some embodiments, the catchers have flat inserts that facilitate conducting a strip stretch or draw test simultaneously with a tensile strip friction test. In other embodiments, the catchers include drawbead inserts that facilitate conducting a drawbead friction test simultaneously with a tensile strip friction test.

20 Claims, 9 Drawing Sheets

(58) Field of Classification Search
CPC ... G01N 2203/0075; G01N 2203/0017; G01N 3/00; G01N 3/08; G01N 19/02
See application file for complete search history.

(56) References Cited

U.S. PATENT DOCUMENTS

| | | | | |
|---|---|---|---|---|
| 5,178,017 | A * | 1/1993 | Dinzburg | G01N 3/20 73/849 |
| 5,507,189 | A * | 4/1996 | Kim | G01N 3/28 73/838 |
| 5,679,883 | A * | 10/1997 | Wedeven | G01N 3/56 73/10 |
| 6,094,967 | A * | 8/2000 | Cavdar | G01N 19/02 73/9 |
| 6,167,745 | B1 * | 1/2001 | Hamer | G01N 19/02 73/9 |
| 7,188,516 | B2 * | 3/2007 | Devlin | G01N 19/02 73/115.02 |
| 7,237,423 | B1 * | 7/2007 | Nagel | B21D 22/26 72/350 |
| 8,177,953 | B2 * | 5/2012 | Nardi | G01N 19/04 205/81 |
| 8,464,591 | B2 * | 6/2013 | Kuwayama | G01N 3/28 73/799 |
| 9,091,617 | B2 * | 7/2015 | Edelman | G01N 3/32 |
| 9,189,592 | B2 * | 11/2015 | Nam | G06F 30/17 |
| 9,354,151 | B2 * | 5/2016 | Clark | G01N 3/20 |
| 9,581,534 | B2 * | 2/2017 | Adams, Jr. | G01N 19/02 |
| 9,784,655 | B2 * | 10/2017 | Heiss-Chouquet | G01N 3/08 |
| 10,048,181 | B2 * | 8/2018 | Aegerter | G01N 3/04 |
| 10,060,840 | B2 * | 8/2018 | Panza-Giosa | G01N 3/20 |
| 10,067,044 | B2 * | 9/2018 | Taba | B64C 1/12 |
| 10,571,376 | B2 * | 2/2020 | Lotze | G01N 3/20 |
| 10,996,150 | B2 * | 5/2021 | Jeong | G01N 3/04 |
| 2007/0256503 | A1 * | 11/2007 | Wong | G01N 3/34 73/812 |
| 2008/0295606 | A1 * | 12/2008 | Chinavare | G01N 3/32 73/849 |
| 2012/0144896 | A1 | 6/2012 | Pham et al. | |
| 2012/0167662 | A1 | 7/2012 | Ardiff et al. | |
| 2013/0205911 | A1 * | 8/2013 | Wang | G01N 3/34 73/812 |
| 2015/0068273 | A1 | 3/2015 | Wolf et al. | |
| 2015/0082860 | A1 * | 3/2015 | Beau | G01N 19/02 73/9 |
| 2017/0023454 | A1 | 1/2017 | Panza-Giosa et al. | |
| 2017/0108387 | A1 * | 4/2017 | Vinogradov-Nurenberg | G01L 5/0061 |

FOREIGN PATENT DOCUMENTS

| | | | | |
|---|---|---|---|---|
| GB | 1550291 | A * | 8/1979 | B21B 39/006 |
| JP | 2963629 | | 6/1996 | |
| JP | 08145876 | A * | 6/1996 | |
| JP | 2003161663 | A * | 6/2003 | |
| JP | 2005329411 | A * | 12/2005 | |
| JP | 2012006038 | A * | 1/2012 | |

OTHER PUBLICATIONS

Supplementary European Search Report for EP patent application No. 19772547, dated Jan. 29, 2021.
Hassan et al., "A Developed Friction Test for Sheet Metal Stretch Forming Process", International Journal of Surface Science and Engineering Available Online at:: https://www.researchgate.net/publication/257527865_A_developed_friction_test_for_sheet_metal_stretch_forming_processes/link/58afe145aca2725b5411393f/download, Jan. 2013, 19 pages.
International Application No. PCT/US2019/022181, International Search Report and Written Opinion, dated May 31, 2019, 6 pages.

* cited by examiner

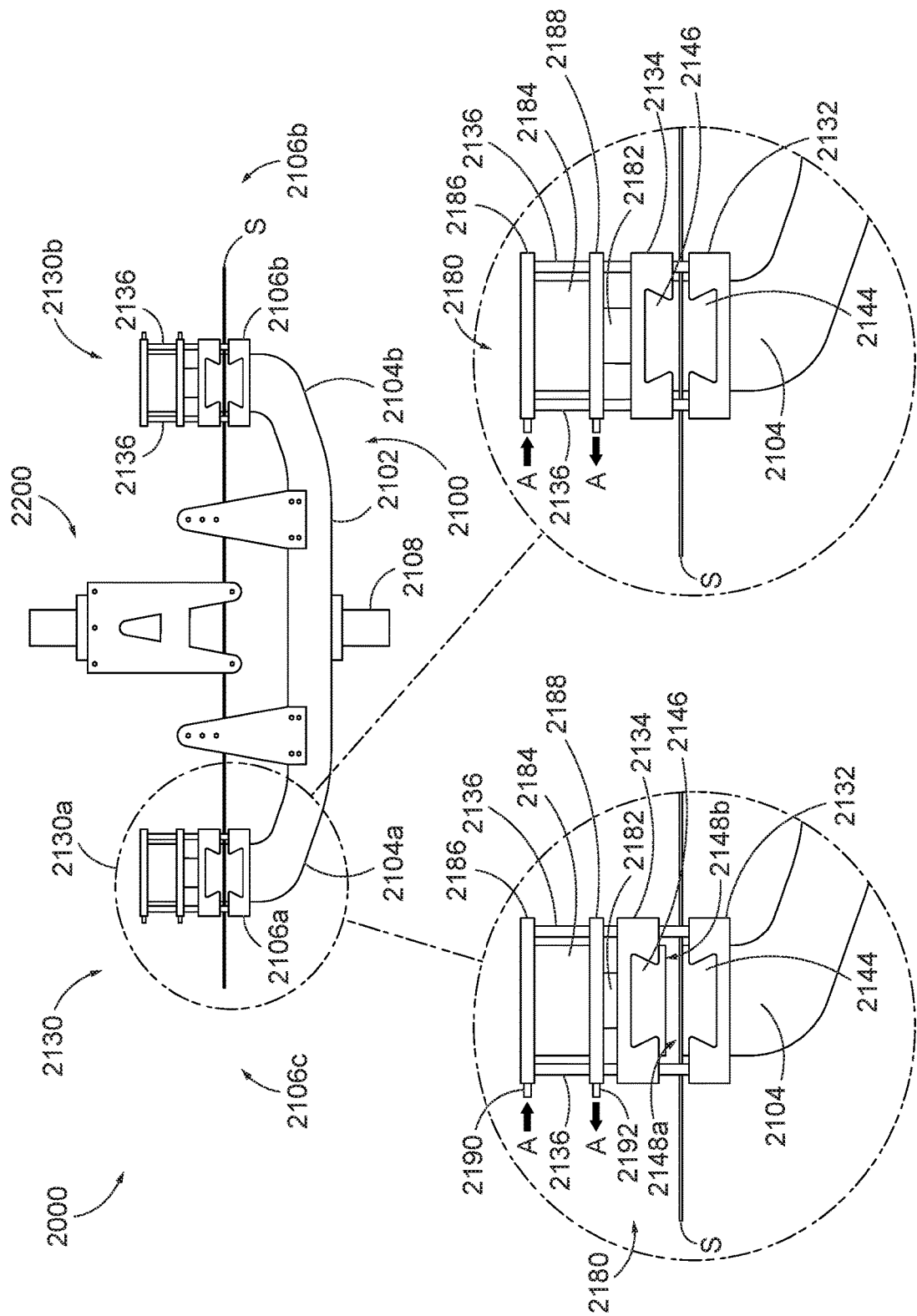

UNIVERSAL STRIP TRIBOLOGICAL SIMULATOR

FIELD OF THE INVENTION

The invention relates to tribology testing simulator devices and methods and, more particularly, to a universal strip tribological simulator that allows a user to take measurements of the strip, in particular for testing sheet metal, under actual stamping conditions. The devices comprise a base having a pair ends, the base further including a catcher disposed at each of the ends and a pair of base pins disposed between the catchers, wherein the catchers include a pair of binder plates where at least one of the binder plates applies a binder force; a punch that articulates relative to the base and includes a pair of punch pins that are inwardly oriented relative to the base pins; and a plurality of sensors for measuring parameters of the tested strip.

BACKGROUND

Tribology is a scientific field that generally concerns friction and the interaction of contacting surfaces in relative motion. Friction and surface interaction impacts manufacturing and the articles produced therefrom. Accordingly, various testing devices or simulators have been developed to measure and model these tribological characteristics.

In some applications, for example, a sheet metal deep drawing process, a workpiece is formed having different tribological characteristics at different regions of the workpiece (e.g., wall, flange, drawbead, etc.). For such applications, technicians may perform a series of tribological tests on a sheet metal specimen that mimics a workpiece to model the tribological characteristics existing at the different regions of the workpiece. FIGS. 1A-1D illustrate devices for various commonly utilized tribological tests, including the tensile strip friction test (FIG. 1A), the draw bead friction test (FIG. 1B), the strip stretch/draw test (FIG. 1C), and the disk sliding test (FIG. 1D). Testing simulators have been developed to carry out one or more of these tribological tests, with some of simulators being configured to conduct a single test and others being configured to conduct more than one test. Simulators that conduct more than one test are referred to as universal testing simulators.

Tensile strip friction testing simulator devices model the strain behavior encountered in a deep drawing operation and capture the interfacial characteristics between the sheet metal specimen and the dies in lip regions of a metal sheet. Tensile strip friction testing devices include a pair of catchers (for example catchers 10 shown in FIG. 1A) that secure an opposing pair of ends of the sheet metal specimen SS that has been pre-deformed around a pair of pins 12 having a radius R to simulate a lip region of the forming dies. The device applies two opposed normal forces $P_1$. One of these normal forces $P_1$ is applied to a plate 14 to which the catchers are attached to hold the ends of the sheet metal specimen SS upwardly. The other normal force $P_1$ downwardly pulls a base 16 upon which the pins 12 are mounted. Application of the two opposed normal forces $P_1$ causes a transverse force $P_2$ to be applied to the sheet metal specimen SS between the pins 12. These simulators also include a pair of extensometers $E_1, E_2$ that measure horizontal and vertical extension in the specimen SS and, with these measurements, these simulators may calculate the friction coefficient between the die and the workpiece, as well as the surface roughness of the deformed sheets.

Draw bead friction testing simulator devices (for example as shown in FIG. 1B) runs a metal sheet specimen SS along guide rollers 18 and due to a pull force $P_3$ pulls or draws the metal sheet specimen SS between a series of pins or beads 20,21 (i.e., drawbeads). These testing devices first measure the pull force $P_3$ required to draw a specimen through a series of cylindrical roller beads 20,21 supported by ball bearings with negligible friction. The distance Y between the outer cylindrical roller beads 20 is variable depending on the bending and unbending simulated. This simulates bending and unbending resistance of the specimen SS under "frictionless" conditions. The draw bead friction testing simulator devices also applies a force $P_4$ to set penetration of a central roller bead 21. Then, the pull force $P_3$ required to draw the specimen SS between fixed beads to simulate "non-frictionless" conditions is measured. The specimen's SS coefficient of friction is determined by comparing the two pull forces required to slide and to bend and unbend the specimen SS under the "frictionless" and "non-frictionless" conditions.

Strip draw testing simulator devices (for example as shown in FIG. 1C) comprise a pair of flat plates 30, 32 (that simulate tooling) through which a specimen SS is drawn or pulled by a drawing force. As the sheet specimen SS (typically with lubricant) is drawn through the plates 30, 32 at a constant and known drawing velocity V, a known contact pressure $P_5$ (i.e., a normal force) is applied to the top plate 30 and then gradually increased. Also, a contact pressure $P_5$ is applied to the bottom plate 32. The strip draw testing simulator measures the drawing force required to pull the specimen SS through the plates 30, 32 and then calculates the coefficient of friction by comparing the drawing force to the normal force.

Technicians sometimes utilize disk sliding test simulator devices (for example as shown in FIG. 1D) for a pin on disk friction test to measure the effectiveness of low friction coatings. Pin on disk testing devices generally comprise a stationary "pin" 40 under an applied load in contact with a rotating disk 42. The pin 40 has a diameter $d_0$ and is fixed at a specified location a distance "R" from the center of the disk 42. The disk 42 having a diameter $D_0$ is rotated at a known velocity w while a normal load $P_6$ is applied to the pin 40 as the pin 40 contacts the disk 42. This simulator calculates the coefficient of friction utilizing the known variables, such as, the applied pressure (normal force), sliding speed, lubricant, location of the pin, etc.

Existing simulators, however, deform their testing specimens in simplified configurations that may not approximate those encountered during manufacture. Additionally, they may otherwise fail to permit testing under actual (or close to actual) manufacturing conditions. For example, tensile strip testing devices model the strain behavior encountered in a deep drawing operation. Thus, they require use of a pre-deformed specimen that may not be an adequate representation of the ultimate workpiece to be manufactured. Draw bead testing devices simulate formation of draw beads in a specimen to measure the friction encountered at those simulated draw beads. However, they do so in isolation (i.e., not in relation to the remainder of the work piece) and may not be an adequate representation.

Conventional simulators do not deform specimens under the actual or near actual manufacturing and/or stamping conditions. Therefore, it is beneficial to provide a universal tribological testing simulator capable of evaluating various surface interactions and calculating the coefficients of friction at various regions of the testing specimen under actual or close to actual stamping conditions.

SUMMARY OF THE INVENTION

The invention provides a tribological testing simulator for measuring friction of a strip specimen. In one embodiment, the tribological testing simulator comprises a base, a punch, and a plurality of sensors. The base may include a first arm and a second arm aligned on a longitudinal axis of the base, each arm having a lateral portion, an upright portion, and an end to define a U-shape, the first arm lateral portion opposed to the second arm lateral portion, the first arm upright portion extending from the first arm lateral portion to the first arm end, the second arm upright portion extending from the second arm lateral portion to the second arm end, wherein the first arm and second arm together define opposed front and rear sides of the base and opposed upper and lower sides. In addition, the base may include a first catcher disposed at said first arm end and a second catcher disposed at said second arm end, wherein each said catcher includes a pair of binder plates, wherein at least one of the binder plates is for applying a binder force to a strip extending from the first catcher to the second catcher. Moreover, the base may include a pair of transverse base pins disposed between the catchers, a first pair of opposed supports for one of said base pins, the first support extending upwardly from opposed front and rear sides of the first arm, a second pair of opposed supports for another of said base pins, the second support extending upwardly from opposed front and rear sides of the second arm.

The punch is arranged to articulate relative to the base to impart a pull force and includes a pair of transverse punch pins that are inwardly oriented relative to the pair of base pins, said punch for articulating from a first position in which the strip is below the base pins and above the punch pins, to a second position in which the strip is below the base pins and above the punch pins but the punch pins are higher than in the first position.

The plurality of sensors are arranged about the simulator and include a load sensor operatively connected to the punch for measuring the pull force, a load sensor operatively connected to at least one of the first and second catchers for measuring the binder force, and at least one sensor focusing on the test strip specimen as it is deformed The at least one sensor focusing on the test strip specimen measure strain and displacement of the test specimen as it is deformed by the simulator. In one or more embodiments, the at least one sensor focusing on the test strip specimen includes a first sensor focusing on a first region between the left catcher assembly and the left base pin, a second sensor focusing on a second region between the left base pin and the left punch pin, and a third sensor focusing on a third region between the left and right punch pins.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

FIGS. 9A-9B are close-up side views of a binder system that may be utilized open and close the catcher assembly of FIG. 6.

DETAILED DESCRIPTION

Figure 1A:
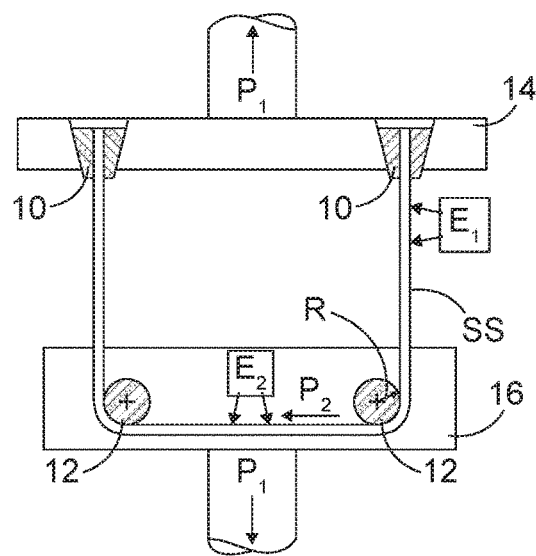
FIGS. 1A-1D are schematic drawings of existing tribological test devices.
Figure 1B:
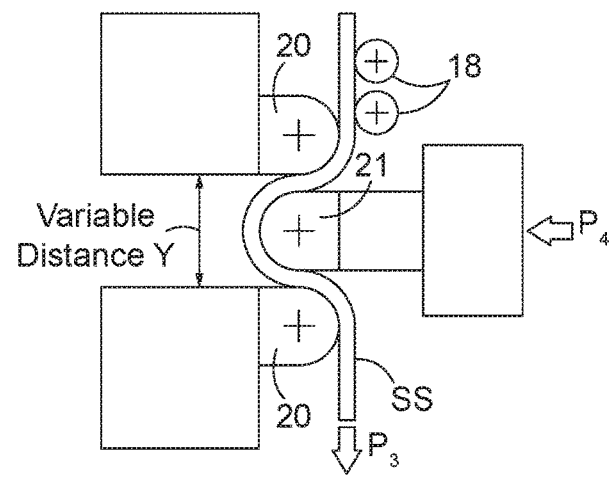
Figure 1C:
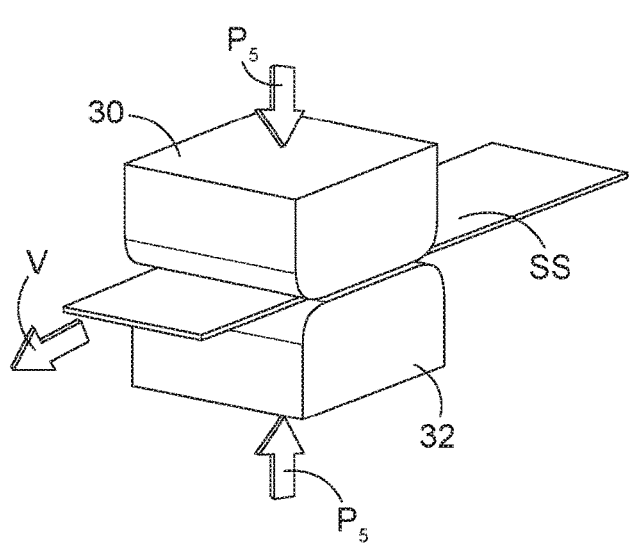
Figure 1D:
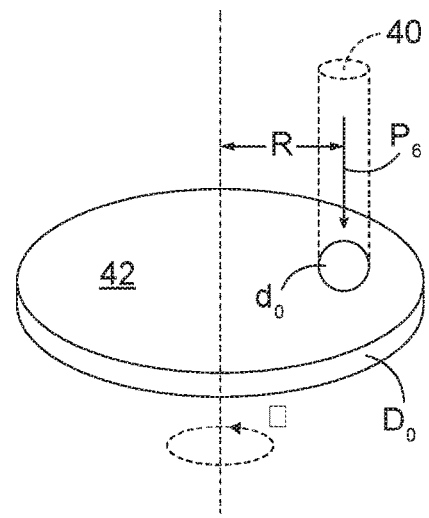

The present invention relates to tribology testing devices and methods and, more particularly, to a universal strip tribological simulator that allows a user to take measurements of the strip under actual stamping conditions.

The strip tribological testing simulator deforms a testing specimen under close-to-real stamping conditions, where the testing specimen represents a blank deformed into a drawn cup shape during the stamping process. The simulator measures simultaneously the forming force and stretch strains of the specimen as it gradually deforms the specimen into a drawn cup shape. With these measurements, the simulator operator may calculate the coefficients of friction.

One example strip tribological testing simulator includes a punch, a pair of punch pins connected to the punch, a base, a pair of catchers connected to the base, a pair of base pins also connected to the base, and a plurality of sensors. The sensors are to measure the forming force and stretch strains of the specimen as the simulator gradually deforms the specimen. The operator secures a specimen between the pair of catchers that, during operation, apply a binder force (or blank holding force) to the specimen and the simulator measures the binder force. This simulates the binder contact interactions experienced by a blank in an actual stamping process. When arranging the specimen within the simulator, the operator positions the pair of punch pins below the specimen to simulate a punch radius; and the operator positions the pair of base pins above the specimen to simulate a die radius. During operation, the punch applies a pull force that the simulator also measures. The plurality of sensors are positioned at one or more regions about the specimen and take measurements as the simulator deforms the specimen in a manner similar to that encountered during a deep drawing process. The simulator communicates with a controller and computer system that, using these measurements, may calculate the coefficients of friction at the various regions of the specimen. These calculations closely approximate actual tribological conditions of a finished workpiece. The present description describes the simulator primarily with reference to sheet metal applications, for example a deep drawn sheet metal blank of aluminum alloy, steel or other metals. However, those skilled in the art will appreciate that the simulator may be used to simulate other processes and be used with other materials.

FIGS. 2-5 are various views illustrating the structure of an example tribological testing simulator 2000 (hereinafter, the simulator 2000) for testing a strip specimen S. Specifically, FIGS. 2-5 respectively illustrate an isometric perspective front view, a front view, a side view, and a top view of the simulator 2000 that may incorporate some or all of the principles of the present disclosure. In addition, the components of the simulator 2000 hereinafter described may be manufactured from any number of materials, for example, metals such as aluminum and steel alloys.

As illustrated, the simulator 2000 may include a base 2100 and a punch 2200. The simulator has a longitudinal (lateral) axis "L", a vertical axis "V" and a transverse axis "T". The base 2100 holds the strip specimen S stationary by applying a pair of binding forces B to the ends of the strip specimen S in an orientation corresponding with the vertical axis V. The binding forces B may be applied by one or more hydraulic, electric or pneumatic actuator systems 102 to which the strip specimen S is functionally attached. In addition, the punch 2200 may exert a pull force P on the strip specimen S along the vertical axis V by a hydraulic, electric or pneumatic actuator system 104, which in turn stretches the specimen S.

The base 2100 is fixed or mounted in place to a support structure 106. In one embodiment, the support structure 106 is a tensile testing machine such as the Instron or MTS testing machine. The strip specimen S is secured to the base 2100 as hereinafter described. The punch 2200 is configured to move relative to the base 2100 for example via the hydraulic, electric or pneumatic actuator system 104 in functional connection to the punch shaft 2202 to provide the load or pull force P to the punch 2200. Accordingly, the base 2100 is stationary relative to the punch 2200 and withstands load or pull force P exerted by the punch 2200 as the punch 2200 pulls upwardly through the strip specimen S. In addition, the punch 2200 or the system 104 may include one or more load sensors $S_P$ that measure pull force P.

Figure 2:
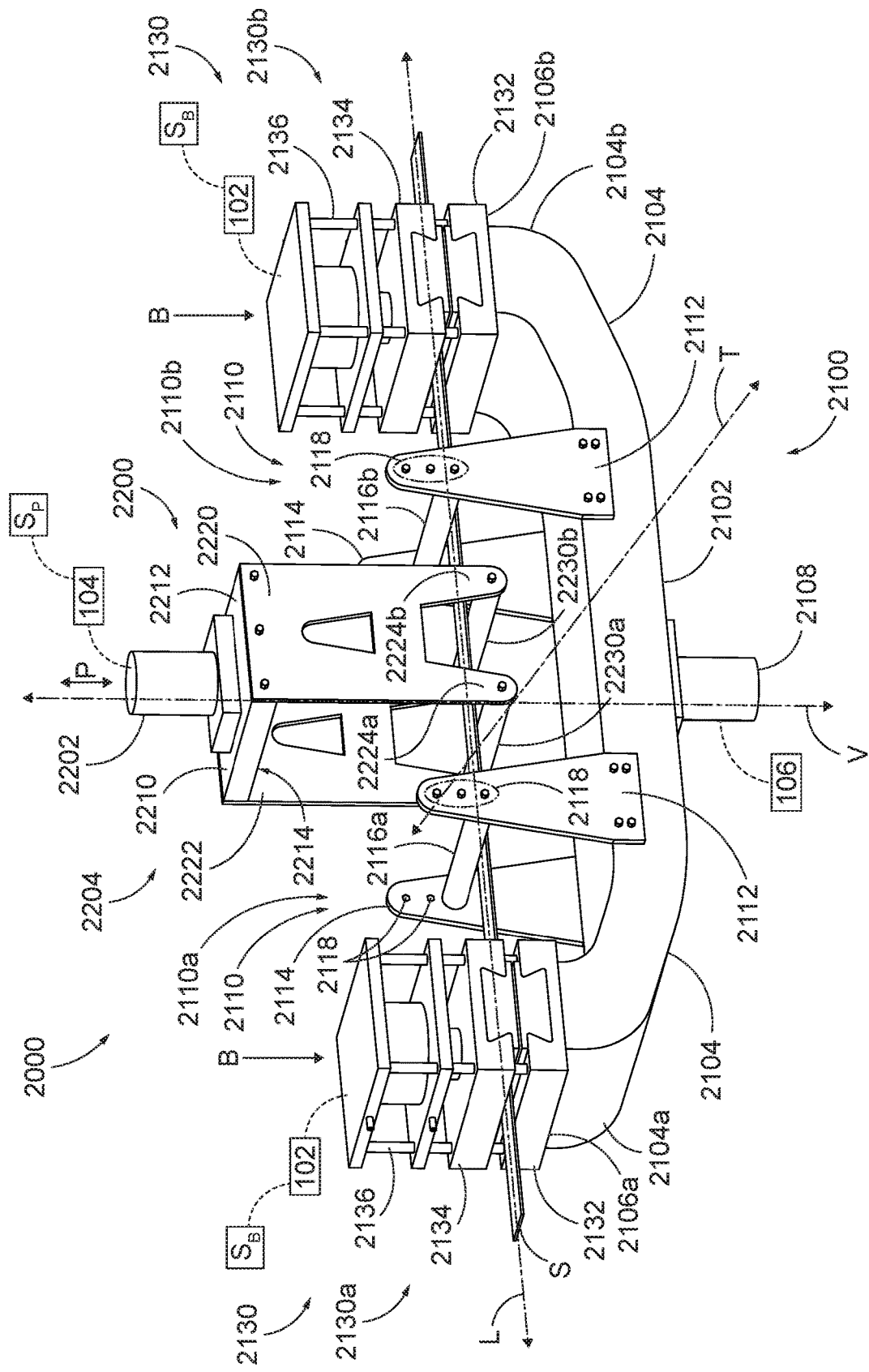
FIG. 2 is an isometric perspective front view of a tribological testing simulator according to one or more embodiments
Figure 3:
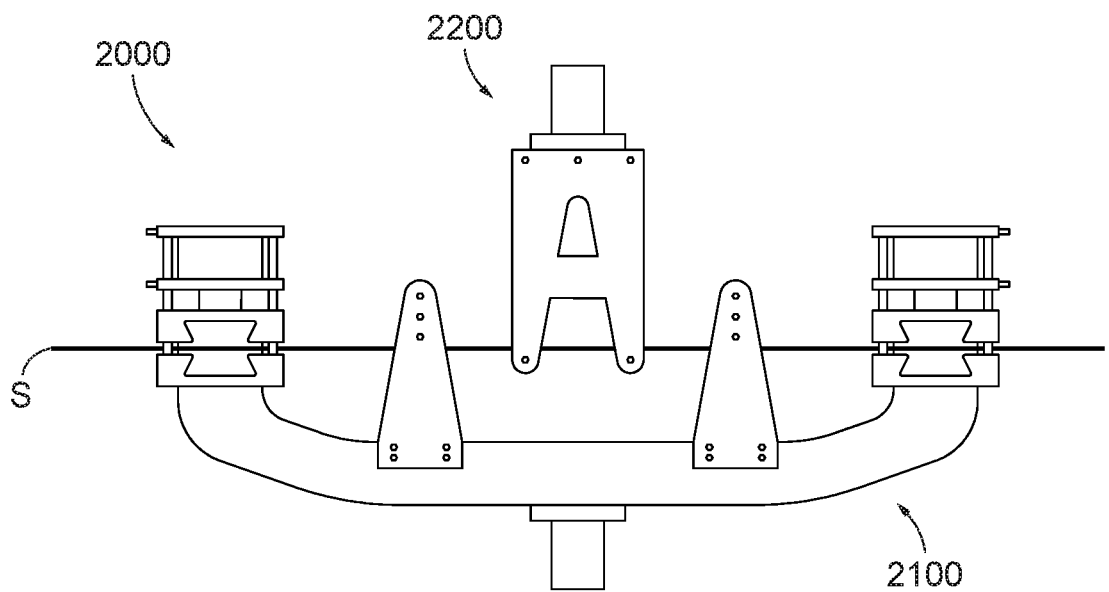
FIG. 3 is a front view of the tribological testing simulator of FIG. 2.
Figure 4:
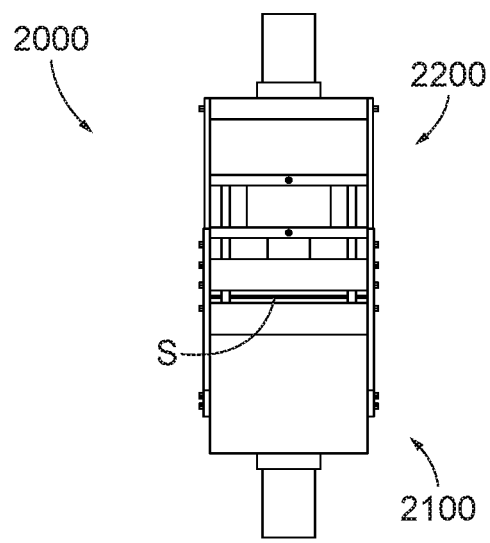
FIG. 4 is a side view of the tribological testing simulator of FIG. 2.
Figure 5:
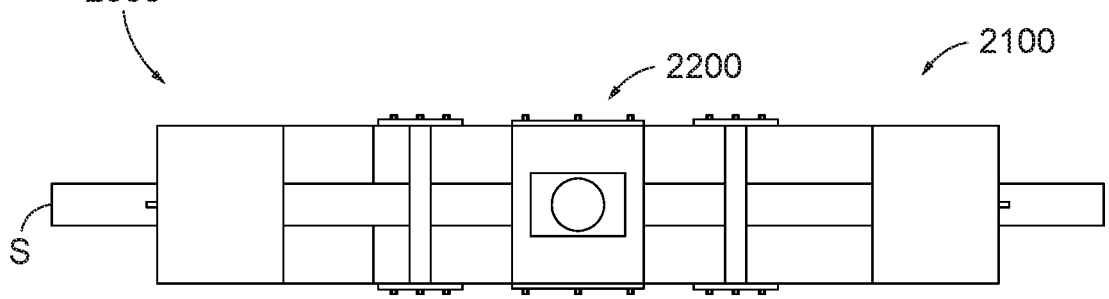
FIG. 5 is a top view of the tribological testing simulator of FIG. 2.

In the illustrated simulator device, the base 2100 is a "U" shaped bracket having a base portion 2102 that interposes a pair of arms 2104. Each arm 2104 has a generally horizontal arm portion 2102a, 2102b, a vertical arm portion 2104a, 2104b extending vertically from the respective horizontal arm portion 2102a, 2102b to a pair of opposing ends 2106a, 2106b of the generally horizontal arm portion, respectively. This disclosure sometimes refers to the vertical arm portion 2104a and the end 2106a as the left arm 2104a and left end 2106a. This disclosure sometimes refers to the vertical arm portion arm 2104b and the end 2106b as the right arm 2104b and right end 2106b. A connector 2108 secures the base 2100 to the support structure 106 which, as mentioned above, may be a testing machine. FIG. 2 illustrates the base 2100 as having a "U" shaped geometry. However, the base 2100 may have other geometries, such as an "I" shaped geometry, without departing from the present disclosure.

FIG. 2 also illustrates first and second base pin assemblies 2110a, 2110b attached to the base 2100. First base pin assembly 2110a is proximate to the left end 2106a. Second base pin assembly 2110b is proximate to the right end 2106b. Accordingly, this description sometimes respectively refers to the pin assemblies 2110a, 2110b as the left and right pin assemblies 2110a, 2110b. The pin assemblies 2110a, 2110b are positioned on the base portion 2102. However, the pin assemblies 2110a, 2110b may be moved closer together (i.e., towards the shaft 2108) or further apart towards their respective ends 2106a, 2106b. As illustrated, each pin assembly 2110a, 2110b includes support comprising a front faceplate 2112 and a rear faceplate 2114 disposed on a respective front and rear faces of the base 2100. In particular, the pin assembly 2110a is supported by a front faceplate 2112 and a rear faceplate 2114 disposed on respective front and rear faces of the horizontal arm portion 2102a. Meanwhile, the pin assembly 2110b is supported by a front faceplate 2112 and a rear faceplate 2114 disposed on respective front and rear faces of the horizontal arm portion 2102b. Here, the front and rear faceplates 2112, 2114 are secured to the base 2100 via a plurality of bolts. In some embodiments, the base 2100 has a plurality of such bolt holes that are laterally spaced apart from each other on the base 2100 such that the front and rear faceplates 2112, 2114 may be positioned in various lateral locations. In other embodiments, the front and rear faceplates 2112, 2114 are removably attached to the base 2100 without bolts to facilitate lateral adjustment.

The pin assemblies 2110a, 2110b also each include one base pin 2116a, 2116b mounted between the front and rear faceplates 2112, 2114. The base pin 2116a arranged within the left pin assembly 2110a is sometimes referred to as a left base pin. The base pin 2116b arranged within the right pin assembly 2110b is sometimes referred to as a right base pin. As mentioned, the base pin assemblies 2110a, 2110b may be positioned at various lateral locations on the base 2100 (i.e., between the ends 2106a, 2106b) to define different die diameters. This is achieved by laterally moving (parallel to the longitudinal axis) one or both of the front and rear faceplates 2112, 2114 nearer or further apart.

In addition, the simulator device 2000 may permit the base pin assemblies 2110 to be vertically adjusted relative to the remainder of the base 2100 to further vary die size and/or binder inclination in any given simulation. For example, the front and rear faceplates 2112, 2114 may have a plurality of vertical hole positions 2118 in which the pins 2116a, 2116b may be positioned. In the illustrated simulator device, the base pins 2116a, 2116b are positioned in the lower most vertical hole positions 2118. However, either or both of the base pins 2116a, 2116b may be arranged in a higher vertical hole position 2118 to vary the inclination of the catcher assembly 2130a, 2130b (i.e., binder inclination) during a simulation, for example, as described below with reference to FIG. 8.

The base pins 2116a, 2116b may have any number or radiuses to further vary the parameters and variables of a given tribological simulation. In some simulations, the left base pin 2116a may have a different radius than the right base pin 2116b. Also, one or both of the base pins 2116a, 2116b may be configured to rotate relative to their respective base pin assembly 2110a, 2110b. If desired, the simulator device may utilize bearings or other devices to reduce or even eliminate friction. For example, the vertical hole positions 2118 may include a lubricant material arranged around their perimeters. This allows the vertical hole positions 2118 to act as sleeve bearings within which a shaft portion of the base pins 2116a, 2116b may rotate. If desired, roller bearings are provided within the vertical hole positions 2118 to facilitate rotation of the base pins 2116a, 2116b therein. It should be appreciated, however, that the simulator device may utilize other means to facilitate frictionless rotation of the base pins 2116a, 2116b within the vertical hole positions 2118 without departing from the present disclosure. Moreover, the base pins 2116a, 2116b may be temperature controlled to vary simulation parameters. For example, the base pins 2116a, 2116b may include heating elements (not illustrated) therein or be resistively heated. The base pins 2116a, 2116b may further include a heat sensor and controller so that their surface temperatures may be set at a desired temperature. The simulator may utilize other heaters to heat the base pins 2116a, 2116b to control their temperature without departing from the present disclosure.

FIG. 2 shows a pair of catcher assemblies 2130a, 2130b attached to the base 2100. For example, first catcher assembly 2130a is proximate to the left end 2106a. Second catcher assembly 2130b is proximate to the right end 2106b. Accordingly, this disclosure sometimes respectively referred to the catcher assemblies 2130a, 2130b as the left and right catcher assemblies. As mentioned above, the catcher assemblies 2130a, 2130b are configured to apply a binder force B to the strip specimen S and secure it relative to the base 2100 during a simulation. The catcher assemblies 2130a, 2130b may be hydraulically powered by an actuator 102 to apply the binder force B. However, the catcher assemblies 2130a, 2130b may include other of means of actuation, for example, pneumatic or electrical motor, to apply the binder force B without departing from the present disclosure. In addition, the catcher assemblies 2130a, 2130b may include one or more load sensors SB operably connected to the actuator 102 to measure the binder force B.

In the illustrated simulator device, first catcher assembly 2130a is attached to the left arm 2104a and the second catcher assembly 2130b is attached to the right arm 2104b. More specifically, the catcher assemblies 2130a, 2130b each include a bottom binder plate 2132 and an upper binder plate 2134. The binder plates 2132, 2134 each include an interior face and an outer face generally oriented such that the interior faces of the binder plates 2132, 2134 face each other. Each binder plate 2132, 2134 is arranged at a respective arm end 2106a, 2106b, with the bottom binder plates 2132 being secured thereto. Each of the upper binder plates 2134 is arranged proximate to and above its respective bottom binder plate 2132 such that the interior faces of the binder plates 2132, 2134 are generally parallel (to each other). In addition, at least one of the binder plates 2132, 2134 is configured to articulate as described below.

Figure 6:
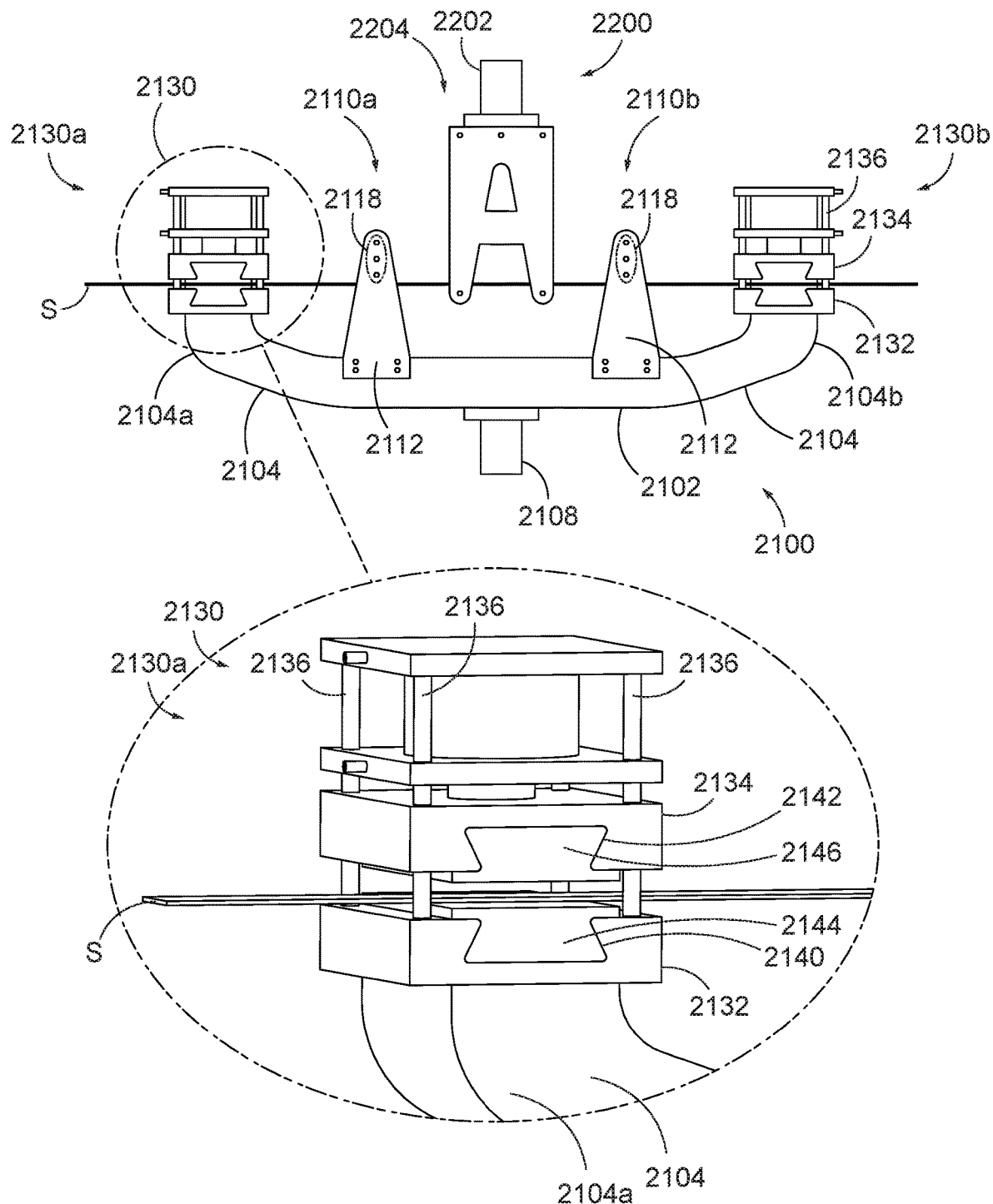
FIG. 6 is a close-up side view of the catcher assembly of the tribological testing simulator of FIG. 2.

FIG. 6 illustrates the left catcher assembly 2130a. The right catcher assembly 2130b may be similarly structured and configured. As illustrated, the catcher assemblies 2130a, 2130b may further include a guide that maintains the binder plates 2132, 2134 in a desired orientation relative to each other. The illustrated simulator device maintains the binder plates 2132, 2134 in a desired orientation relative to each other along a predefined binder plate path via the guide. Thus, the interior faces of the binder plates 2132, 2134 may make substantially complete contact if compressed together (i.e., without an insert having a compression surface as hereinafter described). Here, the guide maintains the binder plates 2132, 2134 in a substantially parallel orientation along the binder plate path.

Where utilized, the guide may include various structures or systems. Here, the guide comprises a plurality of pillars 2136 that extend upward from an interior face of the bottom binder plate 2132 and through the upper binder plate 2134. As illustrated, the plurality of pillars 2136 define the binder plate path on which the upper binder plate 2134 vertically travels relative to the lower binder plate 2132 between a compressed (or closed) position and an uncompressed (or open) position. In the illustrated simulator device, the plurality of pillars 2136 include four (4) pillars (the fourth pillar 2136 is obscured from view) extending upward from the corners of the interior face of the lower binder plate 2132, into and through the interior face of the upper binder plate 2134 at the corners thereof. The plurality of pillars 2136 also extend upward into and through additional componentry and structures as hereinafter described. In other non-illustrated embodiments, the guide may include a pair (or more) of tracks within which the upper binder plate 2134 rides, or a sleeve within which the upper binder plate 2134 rides. If desired, the simulator device has no such guide. For example, the simulator device having no such guide may couple the upper binder plates 2134 to another structure not integral with the base 2100.

In some simulator devices, the interior faces of the binder plates 2132, 2134 include compression surfaces that articulate together as hereinafter described to secure the strip specimen S by squeezing and compressing the strip specimen S. In some simulator devices, these compression surfaces are substantially flat so the compression surfaces of the binder plates 2132, 2134 make substantially complete contact. However, other simulator devices have interior surfaces provided with non-flat textures, contours, or protrusions that, for example, may mimic the draw bead test. In the illustrated simulator devices, the binder plates 2132, 2134 respectively include a lower and upper recess 2140, 2142 arranged to receive a lower and upper insert 2144, 2146, respectively. If desired the lower and upper recess 2140, 2142 are sized and shaped to receive a correspondingly sized and shaped base of the lower and upper inserts 2144, 2146. In the illustrated simulator device, the lower and upper insert 2144, 2146 have a tapered base, and the lower and upper recesses 2140, 2142 are correspondingly sized and shaped to receive the tapered base. It will be appreciated, however, that various types of joints as known in the art may be utilized to secure the lower and upper insert 2144, 2146 within their corresponding one of the recesses 2140, 2142.

Figure 7A:
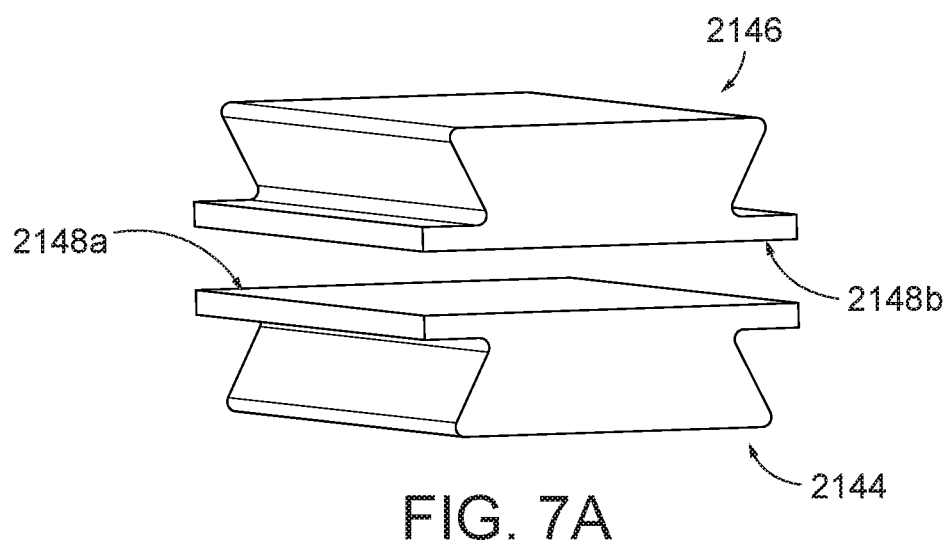
FIGS. 7A-7C are isometric side views of inserts that may be utilized in the catcher assembly of FIG. 6.

FIG. 7A illustrates the lower and upper inserts 2144, 2146, according to one or more simulator devices. As illustrated, the lower and upper inserts 2144, 2146 may be flat inserts having substantially flat contact or compression surfaces 2148a, 2148b. As illustrated, the lower and upper inserts 2144, 2146 are installed within their corresponding recesses 2140, 2142. Also, the compression surfaces 2148a, 2148b are raised above the interior faces of the binder plates 2132, 2134. Thus, the compression surfaces 2148a, 2148b may make complete contact with one another when that they are compressed (or mated) together in parallel orientations. In other simulator devices of the invention, however, the compression surfaces 2148a, 2148b are not raised (i.e., they are level or recessed/sunk) so they make substantially complete contact together with the interior faces of the binder plates 2132, 2134.

In some simulator devices of the invention, either or both of the lower and upper inserts 2144, 2146 may be heated to a certain temperature set by the operator. For example, the lower and upper inserts 2144, 2146 may each include heating elements 2198, 2199 (FIG. 7A) therein connected to a controller that permits selective heating of the lower and upper inserts 2144, 2146. The simulator 2000 may utilize the temperature of the lower and upper inserts 2144, 2146 as additional variables when making tribological calculations as hereinafter described.

Figure 7B:
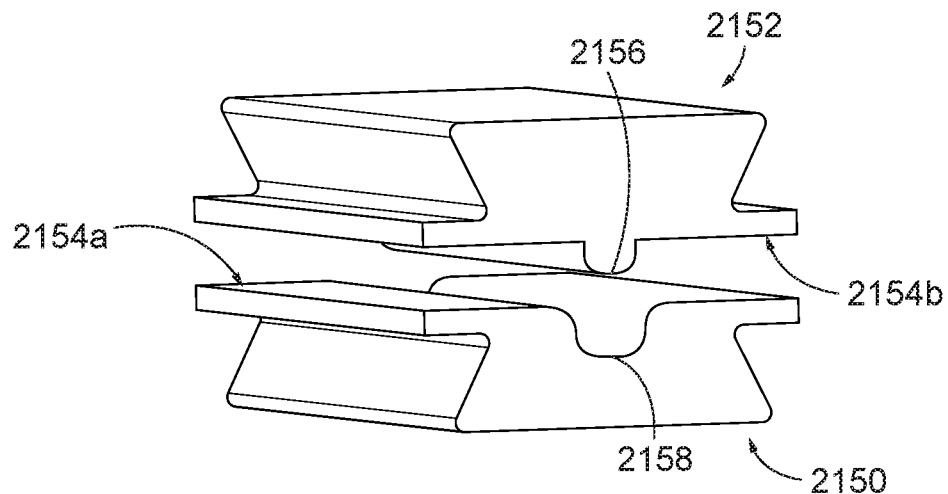

Different inserts may be installed within the lower and upper recesses 2140, 2142 that have different geometries and shapes. FIG. 7B illustrates a single bead lower and upper insert 2150, 2152 that may be respectively installed within the lower and upper recesses 2140, 2142, according to one or more embodiments. Here, each insert 2150, 2152 includes a compression surface 2154a, 2154b. Also, each compression surface 2154b (of the upper insert 2152) includes a bead 2156 that may be inserted into and received within a correspondingly shaped recess 2158 formed into the compression surface 2154a (of the lower insert 2150).

Figure 7C:
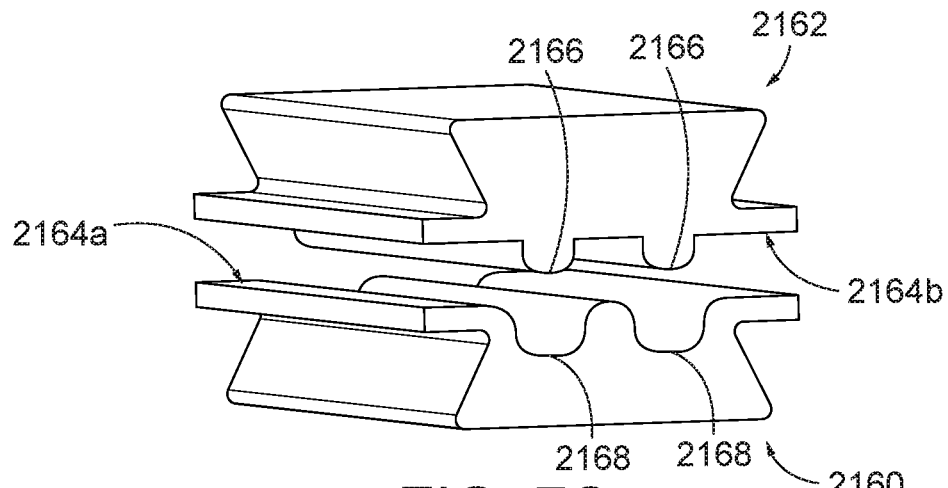

FIG. 7C illustrates a double bead lower and upper insert 2160,2162 that may be respectively installed within the lower and upper recesses 2140,2142, according to one or more embodiments. Here, each insert 2160, 2162 includes a compression surface 2164a, 2164b. Each compression surface 2164b (of the upper insert 2162) includes a pair of beads 2166 that may be inserted into and received within a correspondingly shaped pair of recesses 2168 formed into the compression surface 2164a (of the lower insert 2160). The inserts illustrated in FIGS. 7A-7C are not exclusive. Differently shaped inserts may be utilized depending on the type of tribological test to be performed and the parameters thereof.

Figure 8:
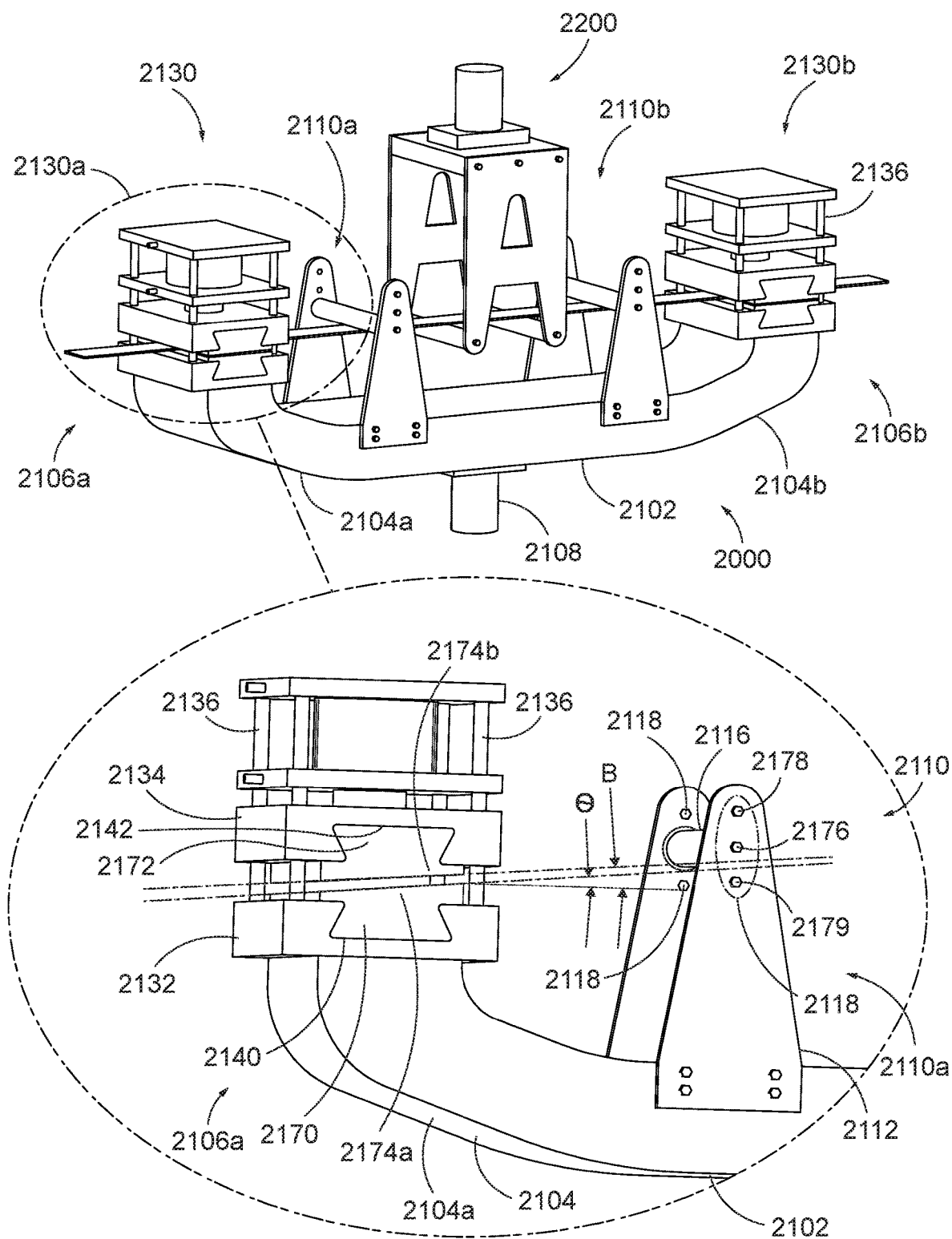
FIG. 8 is a close-up isometric side view of exemplary catcher assembly inclinations that may be utilized with the tribological testing simulator of FIG. 2.

As mentioned above, the specimen S may be oriented within the catcher assemblies 2130a, 2130b in a number of orientations. For example, FIGS. 2-6 illustrate the simulator device 2000 holding the specimen S in a substantially horizontal orientation. However, the specimen S may instead be held within the simulator device 2000 in a non-horizontal orientation. FIG. 8 illustrates a manner in which either or both of the catcher assemblies 2130a, 2130b may hold the specimen S to provide various angular testing conditions (i.e., various binder inclinations. In the illustrated simulator device 2000, a lower angled insert 2170 is installed within the lower recess 2140 of the lower binder 2132, and an upper angled insert 2172 is installed within the upper recess 2142 of the upper binder 2134. The lower and upper angled inserts 2170, 2172 have compression surfaces 2174a, 2174b, respectively, correspondingly angled to mate together as detailed above. The lower and upper angled inserts 2170, 2172 are illustrated as having flat compression surfaces 2174a, 2174b. However, they may be configured differently as detailed above, for example, with a single draw bead, a double draw bead, etc.

In the illustrated simulator device, the compression surfaces 2174a, 2174b of the lower and upper angled inserts 2170, 2172 are angled at a corresponding angle θ. Here, the corresponding angle θ aligns the compression surfaces 2174a, 2174b with the base pin 2116a arranged at a middle position 2176 of the vertical positions 2118. However, the lower and upper angled inserts 2170, 2172 may be provided with different corresponding angles that align with different vertical positions. For example, the compression surfaces 2174a, 2174b may instead be angled at a corresponding angle "B" that aligns with the base pin 2116 when installed in an upper position 2178 of the vertical positions 2118. Here, when the inserts are not angled (for example, as illustrated in FIGS. 7A-7C), they may align with the base pin 2116 when installed at a lower position 2179 of the vertical positions 2118.

Utilizing the angled inserts 2170 in combination with installing the base pins 2116 at the corresponding vertical position 2118 allows the technician to adjust the inclination of the specimen S. Thus, the technician may create an angular testing condition. It will also be appreciated that the base pin assemblies 2110 may include more or less than the three (3) vertical positions 2118. In addition, the technician (operator) may install the strip specimen S within the lower and upper angled inserts 2170, 2172 that do not align with the base pin 2116 as detailed above. Accordingly, the technician may install the base pin 2116 in one of the vertical positions 2118 that is not aligned with the compression surfaces 2174a, 2174b. Also, the technician may perform the simulation when the lower and upper angled inserts 2170, 2172 are aligned with the base pin 2116. For example, the technician may perform a simulation after installing the strip specimen S within the lower and upper angled inserts 2170, 2172 defined by the corresponding angle θ and setting the base pin 2116 in one of the vertical positions 2118 that is not aligned with the compression surfaces 2174a, 2174b thereof (e.g., the upper position 2178 or the lower position 2179).

Various actuators or systems may be utilized to provide one or both of the binder plates 2132, 2134 with the binder force B. As mentioned above, the binder force B is utilized to secure and squeeze the specimen S between the inserts 2144, 2146 installed therein, and one or more load sensors SB may be provided to measure the binder force B as illustrated in FIG. 2. Also, the binder plates 2132, 2134 deform the specimen S as they are driven together with the binder force B in tests utilizing the single bead inserts 2150,2152, the double bead inserts 2160,2162, or other differently shaped inserts. As described below, each of the catcher assemblies 2130 includes a binder pressure system 2180 that provides the binder force B to the upper binder plate 2124. The binder pressure system 2180 drives the upper binder plate 2124 towards the lower binder plate 2132 along the path defined by the plurality of pillars 2136. Thus, the binder pressure system 2180 provides the binder force B to compress the specimen S and deform the strip specimen S in tests where the appropriate inserts are installed. The simulator 2000 measures the binder force B via one or more load sensors SB and utilizes that measurement when making tribological calculations as described below. The one or more load sensors SB may be operably connected to one or both of the binder plates 2132, 2134 to measure the binder force B applied thereby.

FIGS. 9A-9B illustrate a typical binder pressure system 2180, suitable for simulator devices of the present invention. The binder pressure system 2180 may be operably connected to the one or more load sensors SB to measure the binder force B. Here, the binder pressure system 2180 is a hydraulic or pneumatic pressure system having a piston 2182 that reciprocates or slides relative to a cylinder 2184 as the cylinder 2184 is pressurized and de-pressurized. The cylinder 2184 is a container (that may or may not be cylindrically shaped) and includes a base plate 2186 at an upper end thereof and a binder back plate 2188 at a lower end thereof. Thus, the cylinder 2184 interposes the base plate 2186 and the binder back plate 2188. As illustrated, the pillars 2136 extend upward from the upper binder plate 2134, into and through the binder back plate 2188, and into the base plate 2186. The upper binder plate 2134 may travel along the path of the pillars 2136 between a lower position (i.e., where the compression surface 2148b of its insert 2146 is in contact with that of the lower binder plate 2132) and an upper position (i.e., where the outer face of the upper binder plate 2134 is in contact with a contact face of the binder back plate 2188). Accordingly, the binder back plate 2188 provides a backstop for the upper binder plate 2134. This allows the upper binder plate 2134 to travel along the pillars 2136 a distance from the compression surface 2148b (of the lower insert 2144 of the lower binder plate 2132) to the contact face of the binder back plate 2188. In addition, a dampener or bumper (not illustrated) may be provided on the contact face of the binder back plate 2188 and/or on the upper face of the upper binder plate 2134. As will be appreciated, a dampener will operate as a shock absorber and dampen any impact between the upper binder plate 2134 and the binder back plate 2188. Where utilized, the bumper may be made of any number of resilient materials known in the art, including but not limited to, rubber, silicone, etc.

Attached to an end of the piston 2182 at a location within the cylinder 2184 is a closed head (obstructed from view) that slides within the cylinder 2184 in response to pressure changes. The piston 2182 is attached to the closed head and extends therefrom, out of the cylinder 2184. As illustrated, the piston 2182 extends through the contact face of the binder back plate 2188 attached to the cylinder 2184, and connects to the upper face of the upper binder plate 2134. Thus, the upper binder plate 2134 moves with the closed head of the piston 2182 as the cylinder 2184 is pressurized or depressurized.

As mentioned above, the binder pressure system 2180 may utilize pressure to drive the piston 2182 and the upper binder plate 2134 attached thereto, and may therefore include a pressure inlet 2190 and pressure outlet 2192. The pressure inlet and outlets 2190, 2192 may be arranged at various locations about the cylinder 2184 and, in the illustrated embodiment, the pressure inlet and outlets 2190, 2192 are provided on the base plate 2186 and the binder back plate 2188, respectively. Various fluids may be utilized to pressurize the cylinder 2184. Here, in a pneumatic system a volume of air A is utilized to pressurize the cylinder 2184. However, other fluids may be utilized as known in the art, such as water or more viscous hydraulic fluids. For example, the volume of air A enters the pressure inlet 2190 and pressurizes the cylinder 2184. The cylinder 2184 in turn drives the closed head of the piston 2182, the piston 2182, and the upper binder plate 2134 attached thereto towards the lower binder plate 2132 into the closed position with the binder force B, as illustrated in FIG. 9A. Also, as illustrated in FIG. 9B, the volume of air A exits the cylinder 2184 via the pressure outlet 2192 and retracts the closed head of the piston 2182. In turn, this retracts the piston 2182 and the upper binder plate 2134 attached thereto towards the contact face of the binder back plate 2188 into the open position. Once in the open position, the specimen S may be removed and then re-installed from the simulator device 2000.

Figure 10A:
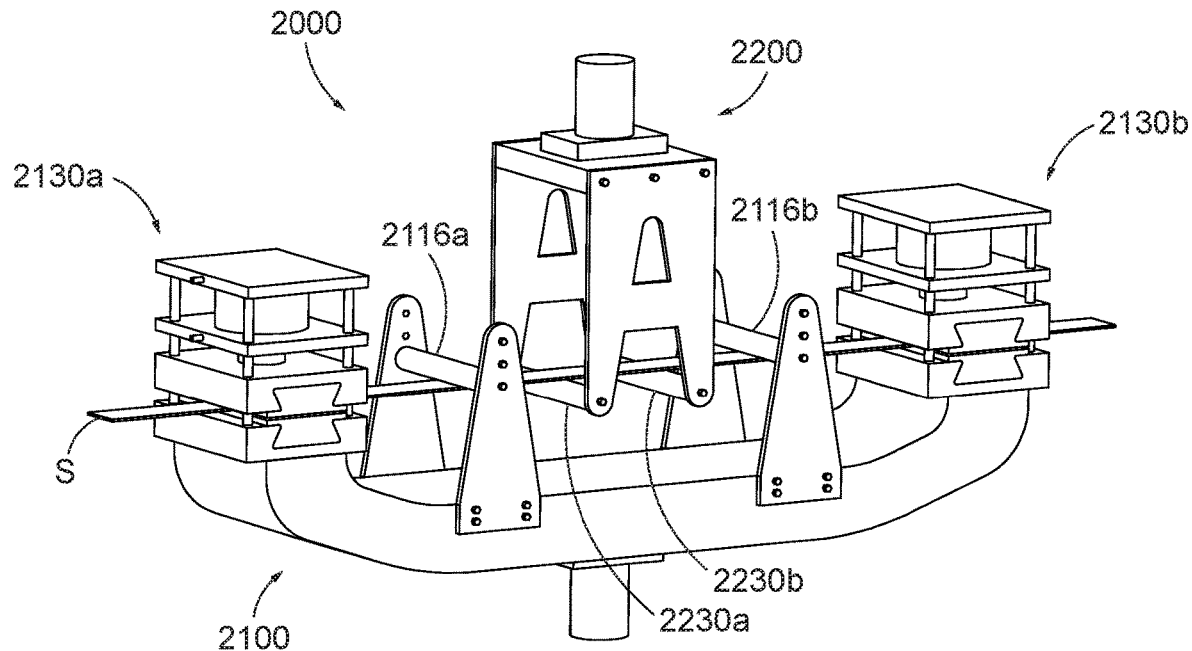
FIG. 10A is an isometric side view of the simulator of FIG. 2 when in an initial set-up position.
Figure 10B:
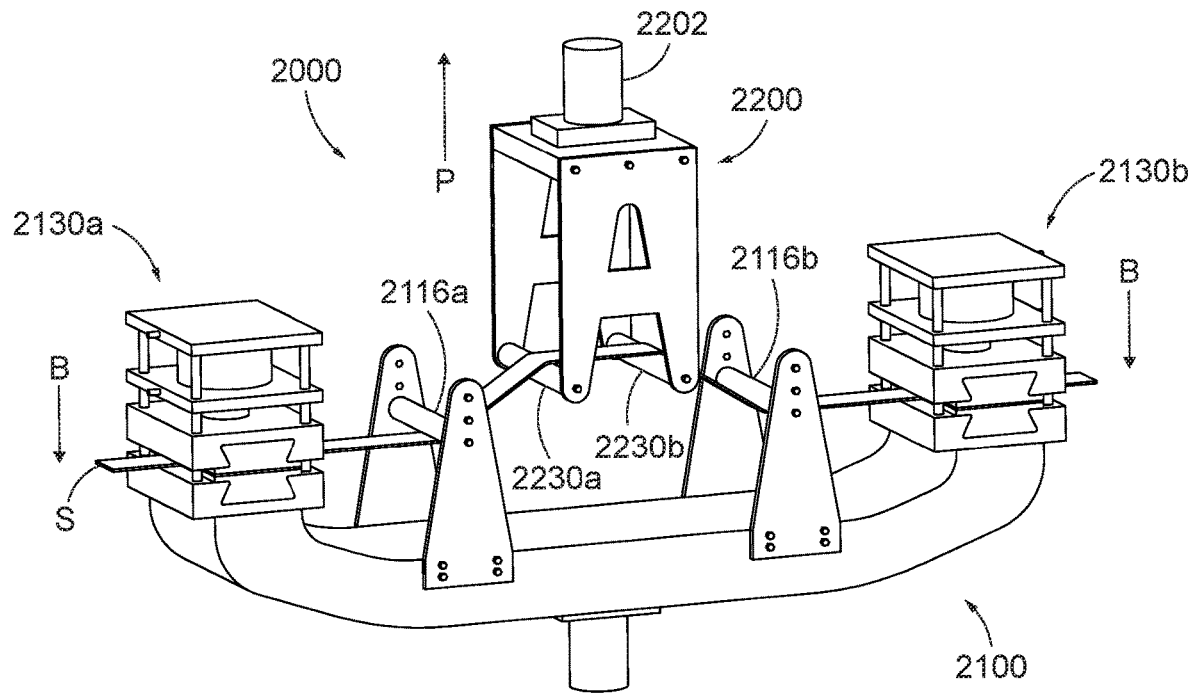
FIG. 10B is an isometric side view of the simulator of FIG. 2 when the punch has been retracted into an exemplary testing position.

As mentioned above, the simulator device 2000 also includes the punch 2200. The punch 2200 may be driven towards the base 2100 into an initial set-up position, and then retracted therefrom into various testing positions. FIG. 10A illustrates the simulator 2000 when the punch 2200 is in an initial set-up position, according to one or more embodiments. FIG. 10B illustrates the simulator 2000 when the punch 2200 has been retracted from the base 2100 into an exemplary testing position, according to one or more embodiments. As illustrated, the specimen S may be installed in the simulator device 2000 when the punch 2200 is in the initial set-up position proximate to the base 2100. Then, the punch 2200 may be pulled away therefrom with the pull force P to deform the strip specimen S. As described below, the simulator device 2000 may conduct various tribological measurements on the strip specimen S as the punch 2200 articulates from the initial set-up position to one or more testing positions.

FIGS. 2-5 and 10A-10B illustrate various views of the structure of the punch 2200 suitable for use in the simulator device of the present invention. As illustrated, the punch 2200 includes the punch shaft 2202 coupled to an actuator 104. The actuator drives the punch 2200 into the initial set-up position where the strip specimen S may be installed, and then pulls the punch 2200 into various testing positions. As the actuator 104 (FIG. 2) pulls the punch 2200, the punch 2200 deforms the strip specimen S. The actuator 104 may be a hydraulic, pneumatic or electric motor powered system. However, various other actuators may be utilized without departing from the present disclosure.

The punch 2200 also includes punch pin assembly 2204. The punch pin assembly 2204 simulates a punch diameter. Thus, differently sized punch pin assemblies 2204 may be installed on the punch shaft 2202 to simulate different punch diameter sizes. In addition, the punch pin assembly 2204 may be adjustable to simulate a range of punch diameters. In such embodiments, a single punch pin assembly 2204 may be utilized for various tests without having to exchange or swap the punch pin assembly 2204. For example, the punch pin assembly 2204 may be laterally extendible to so that the operator may adjust it between different punch diameters without uninstalling the punch pin assembly 2204.

The illustrated punch pin assembly 2204 comprises a top plate 2210, a pair of plates 2220, 2222, and a pair of punch pins 2230*a*, 2230*b*. The top plate 2210 includes an upper and lower face 2212, 2214. In addition, the pair of punch pins 2230*a*, 2230*b* includes a first (or left) punch pin 2230*a* and a second (or right) punch pin 2230*b*. Moreover, each of the pair of plates 2220, 2222 includes a pair of legs 2224*a*, 2224*b* arranged to secure the punch pins 2230 as hereinafter described. Here, the legs 2224*a*, 2224*b* extend down from their respective plate 2220, 2222. Thus, the left leg 2224*a* of the (first) plate 2220 is disposed proximate to the left leg 2224*a* of the (second) plate 2222, thereby securing the left punch pin 2230*a* there-between. Similarly, the right leg 2224*b* of the (first) plate 2220 is disposed proximate to the right leg 2224*b* of the (second) plate 2222, thereby securing the right punch pin 2230*b* there-between.

As with the base pins 2116 (in FIGS. 10A and 10B referred to as base pins 2116*a*, 2116*b*), the punch pins 2230*a*, 2230*b* may have various radii. In some embodiments, the radius of the first punch pin 2230*a* may be different from the radius of the second punch pin 2230*b*. Also, the legs 2224*a*, 2224*b* may be arranged to quickly detach and replace the punch pins 2230 without exchanging the entire punch pin assembly 2204. In addition, either or both of the punch pins 2230 may be configured to rotate as described above with reference to the base pins 2210. Moreover, the punch pins 2230 may be temperature controllable as described above with reference to the base pins 2210. Even further, the punch pin assembly 2204 may be arranged such that it permits the technician to change the distance spanning between the upper pair of pins 2230 (i.e., between the legs 2224*a*, 2224*b*) to change the simulated punch diameter.

The punch pin assembly 2204 is attached to the punch shaft 2202. The punch shaft 2202 is attached to the upper face 2212 of the top plate 2210. If desired, the punch shaft 2202 is permanently attached to the top plate 2210, for example via welding, mechanical fastening, or adhesive. However, if desired the top plate 2210 is removably attached to the punch shaft 2202, for example by a threaded connection or various other devices and/or materials without departing from the present disclosure.

FIG. 10A shows the pair of plates 2220, 2222 (of the punch pin assembly 2204) each arranged to secure the punch pins 2230*a*, 2230*b* substantially parallel with the base pins 2116*a*, 2116*b*. In addition, the pair of plates 2220, 2222 are arranged to orient the punch pins 2230*a*, 2230*b* in a vertical position below the vertical position of the base pins 2116*a*, 2116*b* (at least when the simulator 2000 is in the initial set-up position). Accordingly, the technician (operator) may feed the specimen S through the catcher assemblies 2130 (i.e., when unclamped), below the base pins 2116*a*, 2116*b*, and above the punch pins 2230. More specifically, the technician may install the specimen S by the following sequential steps: (i) feed the specimen S into the left catcher assembly 2130*a* between its (open) binder plates 2132, 2134; pass the specimen S beneath the left base pin 2116*a*; pass the specimen S above the left and right punch pins

2230a, 2230b; pass the specimen S beneath the right base pin 2116b; and pass the specimen S into the right catcher assembly 2130b, between its (open) binder plates 2132, 2134.

Figure 11:
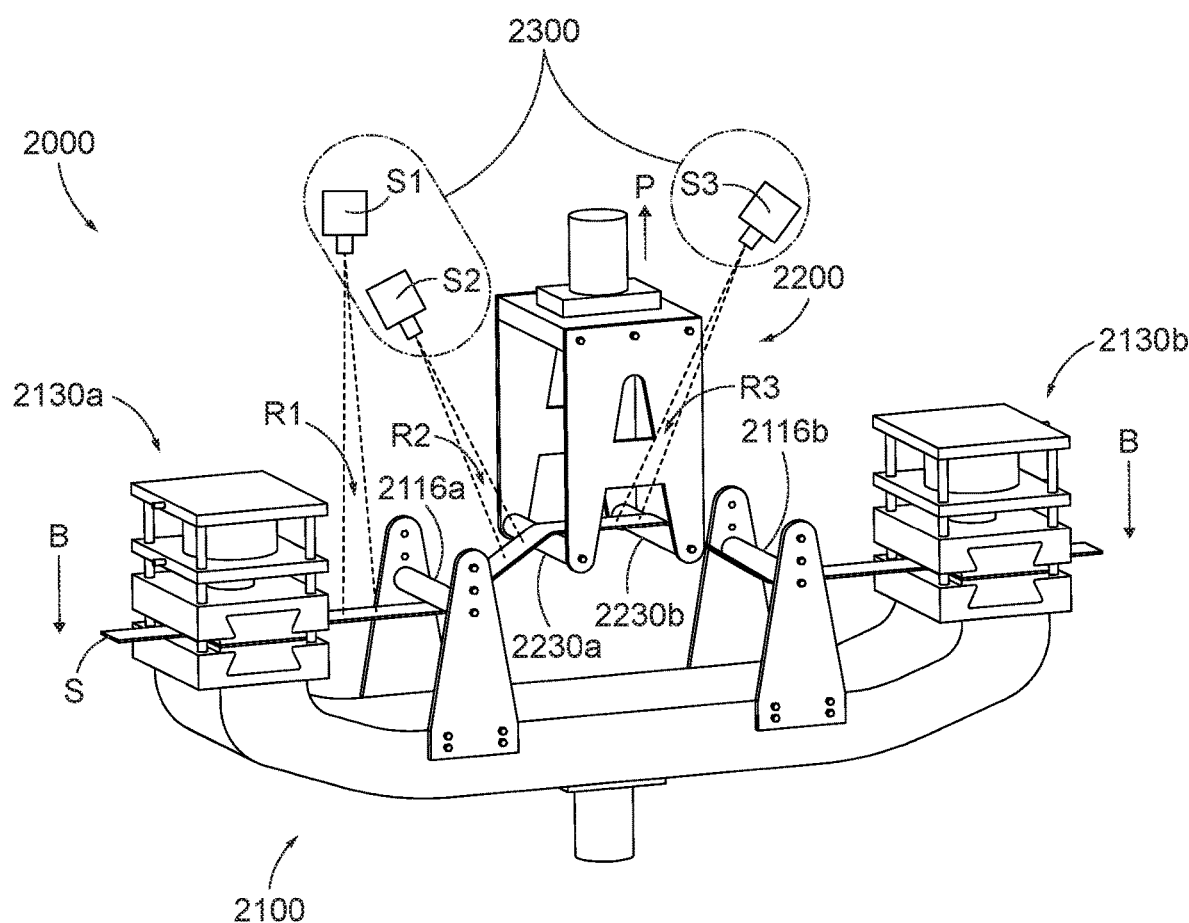
FIG. 11 is an isometric side view of the simulator of FIG. 2 that includes a plurality of sensors arranged thereabout.

As previously mentioned, the simulator device 2000 also includes a plurality of sensors. FIG. 11 illustrates a typical plurality of sensors 2300 comprising a first sensor S1, a second sensor S2, and a third sensor S3. The sensors S1, S2, S3 each focus on a respective region of the strip specimen S corresponding to a contact between the tooling and the specimen S where the frictional effect exists, and FIG. 11 illustrates a typical arrangement of the sensors S1, S2, S3 each focusing on a respective first region R1, second region R2, and third region R3. Here, the first region R1 is a portion of the strip specimen S between the left catcher assembly 2130a and the left base pin 2116a. The second region R2 is a portion of the strip specimen S between the left base pin 2116a and the left punch pin 2230a. The third region R3 is a portion of the strip specimen S between the left and right punch pins 2230a, 2230b. The regions R1, R2, R3 may be differently disposed, however. For example, the first region R1 may be defined as the area between the right catcher assembly 2130b and the right base pin 2116b, and the second region R2 may be defined as the area between the right base pin 2116b and the right punch pin 2230b. Moreover, one or more additional sensors (i.e., in addition to the sensors S1, S2, S3) may be focused on one or more additional regions (i.e., in addition to the regions R1, R2, R3) to provide the simulator device 2000 with even more data.

The sensors S1, S2, S3 each measure the strip specimen S as the punch 2200 deforms it (with the pull force P) into an exemplary testing position such as that illustrated in FIG. 10B. In the illustrated embodiment, the sensors S1, S2, S3 are optical extensometers controlled by a digital image correlation ("DIC") system (not illustrated), as known in the art. More specifically, the sensors S1, S2, S3 may be optical extensometers that utilize high-resolution charge-couples device ("CCD") cameras (e.g., 2 to 12 megapixels), and are focused on a respective region R1, R2, R3 of the strip specimen S. In other embodiments, however, the sensors S1, S2, S3 are optical extensometers that utilize complementary metal oxide semiconductor ("CMOS") technology. In even other embodiments, the sensors S1, S2, S3 are a combination of both CCD and CMOS image sensors.

Regardless of whether the sensors S1, S2, S3 are CCD and/or CMOS image sensors, they convert light into electrons for data collection and post-processing to calculate the strain and displacement values. Thus, the DIC system is a non-contact optical measurement system having one or more digital cameras with sensors that measures strain and displacement in 3D at each of the respective regions R1, R2, R3 subject to the pull force P. In one embodiment, the sensors S1, S2, S3 are ARAMIS (TM) 3-D motion and deformation sensors from GOM. In another embodiment, the sensors S1, S2, S3 are AVE 2 noncontacting video extensometers controlled by the AVE 2 dynamic strain measurement and control system from Instron. In even other embodiments, the sensors S1, S2, S3 are real time strains sensor videoextensometers from Dantec Dynamics.

However, the sensors S1, S2, S3 may comprise other instruments (or combinations of instruments) in addition to or in lieu of the above such as, for example, displacement sensors, lasers trackers, linear variable differential transformers, draw wire sensors, accelerometers, strain gauges, extensometers, clip gauges, profilometers, etc. If desired, the simulator 2000 may be automated and include a controller (not illustrated) that synchronizes its various sensors (e.g., synchronizes the sensors 2300 with the load sensors that measure the pull force P and binder force B) with the various actuation systems that clamp the catcher assemblies 2130 and drive the punch 2200. Such automated simulators 2000 may perform one or more simulations with minimal technician input.

The DIC system may include a controller (not illustrated) that synchronizes various aspects of the simulator 2000. For example, the controller may control operation of the punch 2200 and measurement of the pull force P, operation of the catcher assemblies 2130 and measurement of the binder force B, and operation of the sensors S1, S2, S3 at automatic or technician defined intervals. The DIC system may further include a computer or other medium on which the data is saved, and may be utilized to conduct tribological calculations and/or for other post-processing. Once a simulation is finished, the technician may install another test specimen S into the simulator device 2000 and test it without any additional calibration of the DIC system. It will be appreciated that, while the simulator device 2000 is illustrated with three (3) sensors S1, S2, S3 measuring the respective regions R1, R2, R3, more or less than three (3) of the same or different type of sensors 2300 may be utilized to measure the same or different regions. For example, additional sensors 2300 may be included to measure one or more additional regions of the specimen S in addition to the regions R1, R2, R3.

In one example simulation, the simulator device 2000 simultaneously performs the tensile strip friction test and the strip stretch/draw test. Prior to running this simulation, the technician installs the flat inserts (e.g., the lower and upper inserts 2144, 2146 of FIG. 7A with or without the optional heating elements shown in FIG. 7A) within the catcher assemblies 2130. The technician may then secure the (undeformed) strip specimen S within the simulator 2000 when the punch 2200 is in the initial set-up position illustrated in FIG. 10A. Once the specimen S is properly clamped within the catcher assemblies 2130 with binder forces B, the simulation may begin. The sensors S1, S2, S3 may each begin to measure their respective region R1, R2, R3 of the (undeformed) specimen S when the simulator 2000 is still in the initial set-up position. With the sensors S1, S2, S3 continuously measuring their respective regions R1, R2, R3, the simulator 2000 then begins to draw or pull the punch 2200 (and the punch pins 2230 attached thereto) upward with the pull force P, thereby gradually deforming or drawing the specimen S into a cup shape or deformed state as illustrated in FIG. 10B. During this simulation, the sensors S1, S2, S3 (FIG. 11) each simultaneously measure the displacements and strain gradients of their respective regions R1, R2, R3. This data, together with the known pull force P and binder force B, may then be utilized to calculate tensile strip friction and the strip stretch/draw simulated at the regions R1, R2, R3 under conditions simulating those that occur during an actual stamping process.

In a second example simulation, the simulator 2000 performs simultaneously the tensile strip friction test and the draw bead friction test. Prior to running this simulation, the technician installs drawbead inserts (e.g., the single bead lower and upper insert 2150, 2152 (FIG. 7B), the double bead lower and upper insert 2160, 2162 (FIG. 7C), or both, within the catcher assemblies 2130. In some simulations, the technician may install a drawbead insert of a first type (e.g., the single bead lower and upper insert 2150, 2152) within the left catcher assembly 2130a, and install a drawbead insert of a second type (e.g., the double bead lower and upper insert 2160, 2162) within the left catcher assembly 2130b. After installing the appropriate drawbead inserts and when the simulator 2000 is in the initial set-up position, the technician places the (undeformed) specimen S within the catcher assemblies 2130 that are unclamped and the simulation may begin with the sensors S1, S2, S3 each measuring their respective region R1, R2, R3. The catcher assemblies 2130 clamp the strip specimen S with the binder force B, which deforms the strip specimen S within the drawbead inserts. With the sensors S1, S2, S3 continuously measuring their respective regions R1, R2, R3 as the catcher assemblies 2130a, 2130b compress the specimen S, the simulator device 2000 then begins to draw or pull the punch 2200 (and the punch pins 2230a, 2230b attached thereto) upward with the pull force P. This gradually deforms or draws the specimen S into a cup shape or deformed state as illustrated in FIG. 10B. During this simulation, the sensors S1, S2, S3 each simultaneously measure the displacements and strain gradients of their respective regions R1, R2, R3. This data, together with the known pull force P and binder force B, may then be utilized to calculate tensile strip friction and the strip stretch/draw simulated at the regions R1, R2, R3 under conditions mimicking those that occur during an actual stamping process.

In even other exemplary simulations, the tensile strip friction test, the strip stretch/draw test, and the drawbead test are all performed individually in succession (one after another) or simultaneously.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A tribological testing simulator for measuring friction of a test strip specimen, the simulator comprising:
    a base comprising:
        a first arm and a second arm aligned on a longitudinal axis of the base, each arm having a lateral portion, an upright portion, and an end to define a U-shape, the first arm lateral portion opposed to the second arm lateral portion, the first arm upright portion extending from the first arm lateral portion to the first arm end, the second arm upright portion extending from the second arm lateral portion to the second arm end, wherein the first arm and second arm together define opposed front and rear sides of the base and opposed upper and lower sides,
        a first catcher disposed at said first arm end and a second catcher disposed at said second arm end, wherein each said catcher includes a pair of binder plates, wherein at least one of the binder plates is for applying a binder force to the test strip specimen extending from the first catcher to the second catcher,
        a pair of transverse base pins disposed between the catchers, a first pair of opposed supports for one of said base pins, the first support extending upwardly from opposed front and rear sides of the first arm, a second pair of opposed supports for another of said base pins, the second support extending upwardly from opposed front and rear sides of the second arm;
    a punch actuatable to impart a pull force relative to the base and includes a pair of transverse punch pins that are inwardly oriented relative to the pair of base pins, said punch for articulating from a first position in which the test strip specimen is below the base pins and above the punch pins, to a second position in which the test strip specimen is below the base pins and above the punch pins but the punch pins are higher than in the first position; and
    a plurality of sensors measuring the test strip specimen as it is deformed, the plurality of sensors including a load sensor operatively connected to the punch for measuring the pull force, a load sensor operatively connected to at least one of the first and second catchers for measuring the binder force, and at least one sensor configured to measure displacement or strain of the test strip specimen as it is deformed at one or more regions of the simulator.

2. The tribological testing simulator of claim 1, wherein the pair of base pins are disposed on the base and separated by a die distance, and wherein either or both of the pair of base pins is adjustable on the longitudinal axis to increase or decrease the die distance.

3. The tribological testing simulator of claim 1, wherein the pair of punch pins are disposed on the punch and separated by a punch distance measurable relative to the longitudinal axis, and wherein either or both of the pair of punch pins is adjustable to increase or decrease the punch distance.

4. The tribological testing simulator of claim 1, wherein the pair of punch pins are provided in a punch pin assembly, wherein the punch pin assembly includes a top plate and a pair of opposed actuator side plates that extend down from the top plate, and wherein the pair of punch pins are arranged between the pair of actuator side plates, each said punch pin extending transversely over an upper surface of the the base from one said actuator side plates to another said actuator side plates.

5. The tribological testing simulator of claim 1, wherein the punch includes a hydraulic actuator.

6. The tribological testing simulator of claim 1, wherein the catchers are catcher assemblies that further include:
 an upper and lower binder plate that each include an interior face;
 a plurality of pillars that are attached to the lower binder plate and extend from the interior face of the lower binder plate into the interior face of the upper binder plate and through the upper binder plate; and
 an actuator that drives the upper binder plate along the plurality of pillars.

7. The tribological testing simulator of claim 6, wherein the interior faces of the upper and lower binder plates comprise respective heating elements.

8. The tribological testing simulator of claim 6, wherein the interior faces of the upper and lower binder plates each include a recess and the catcher assemblies further comprise a pair of corresponding inserts received within the recesses, wherein the corresponding inserts each further comprise a compression surface.

9. The tribological testing simulator of claim 8, wherein the compression surface of a first of the corresponding inserts includes a bead and the compression surface of a second of the corresponding inserts includes a correspondingly shaped recess.

10. The tribological testing simulator of claim 8, wherein the compression surface of a first of the corresponding inserts includes a double bead and the compression surface of a second of the corresponding inserts includes a correspondingly shaped recess.

11. The tribological testing simulator of claim 8, wherein the compression surfaces of the corresponding inserts comprise respective heating elements.

12. The tribological testing simulator of claim 8, wherein the compression surfaces of the corresponding inserts are correspondingly angled relative to a horizontal axis.

13. The tribological testing simulator of claim 12, wherein each of the base pins are included in a respective pin assembly,
 each pin assembly comprising one said base pin and the respective pair of supports for the one said base pin, wherein each said pair of supports includes a front faceplate and rear faceplate respectively arranged on a front and rear of the respective arm, each said transverse base pin extending transversely over an upper surface of the base from one said front faceplate to one said rear faceplate,
 wherein the front and rear faceplates each having a plurality of base pin positions,
 wherein the base pins are arranged between the front and rear faceplates within a corresponding pair of the pin positions such that each opposed end of each base pin engages one of the faceplates.

14. The tribological testing simulator of claim 6, wherein each of the catchers are actuated via a binder system, the binder system comprising: a cylinder and a piston disposed within the cylinder, the piston extends from an open end of the cylinder and connects to an upper face of the upper plate, wherein the piston reciprocates the upper binder plate as the cylinder is pressurized by pneumatic or hydraulic pressure within the cylinder.

15. The tribological testing simulator of claim 14, wherein the cylinder includes a pressure inlet and a pressure outlet.

16. The tribological testing simulator of claim 14, wherein the binder system further includes a binder back plate disposed at the open end of the cylinder, the binder back plate including a plurality of openings through which the piston and the plurality of pillars extend.

17. The tribological testing simulator of claim 16, wherein the binder back plate includes a contact face that is oriented towards the upper face of the upper plate, and wherein a dampener is provided on the contact face of the binder back plate.

18. The tribological testing simulator of claim 16, wherein the cylinder includes a pressure inlet and a pressure outlet, wherein the pressure outlet is disposed in the binder backplate.

19. The tribological testing simulator of claim 16, wherein the binder system further includes a base plate on which the cylinder is attached, and wherein the plurality of pillars are attached to and terminate at the base plate.

20. The tribological testing simulator of claim 19, wherein the cylinder includes a pressure inlet and a pressure outlet, wherein the pressure inlet is disposed in the base plate.

* * * * *